US011376365B2

(12) United States Patent
Rekaya et al.

(10) Patent No.: US 11,376,365 B2
(45) Date of Patent: Jul. 5, 2022

(54) HOUSING FOR AN INJECTION DEVICE

(71) Applicant: Sanofi-Aventis Deutschland GMBH, Frankfurt am Main (DE)

(72) Inventors: Naceur Rekaya, Warwick (GB); Neal Alexander Blundred, Warwick (GB); Paul Richard Draper, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 864 days.

(21) Appl. No.: 16/320,519

(22) PCT Filed: May 3, 2017

(86) PCT No.: PCT/EP2017/060508
§ 371 (c)(1),
(2) Date: Jan. 25, 2019

(87) PCT Pub. No.: WO2017/191177
PCT Pub. Date: Nov. 9, 2017

(65) Prior Publication Data
US 2019/0269855 A1 Sep. 5, 2019

(30) Foreign Application Priority Data
May 3, 2016 (EP) .................................... 16168067

(51) Int. Cl.
*A61M 5/24* (2006.01)
*A61M 5/315* (2006.01)
(Continued)

(52) U.S. Cl.
CPC ............ *A61M 5/2422* (2013.01); *A61M 5/20* (2013.01); *A61M 5/24* (2013.01);
(Continued)

(58) Field of Classification Search
CPC .. A61M 5/2422; A61M 5/31585; A61M 5/24; A61M 5/3155; A61M 5/20;
(Continued)

(56) References Cited

U.S. PATENT DOCUMENTS 6,090,082 A * 7/2000 King ....................... A61M 5/24
604/234
2009/0254043 A1* 10/2009 Van .................... A61M 5/31585
604/207
2015/0073350 A1* 3/2015 Einwachter ............. A61M 5/24
604/187

FOREIGN PATENT DOCUMENTS

EP 0937474 8/1999
WO WO 2004/078239 9/2004
(Continued)

OTHER PUBLICATIONS

International Preliminary Report on Patentability in International Application No. PCT/EP2017/060508, dated Nov. 6, 2018, 9 pages.
(Continued)

*Primary Examiner* — Nathan R Price
*Assistant Examiner* — Anh Bui
(74) *Attorney, Agent, or Firm* — Fish & Richardson P.C.

(57) ABSTRACT

A housing includes a body and a cartridge holder. The body can accommodate a drive mechanism including a piston rod to operably engage with a piston of a cartridge filled with a liquid injectable medicament. The cartridge holder has a cartridge receiving space. The cartridge holder has an insert section at a proximal end. The body has a receptacle to receive the insert section. The cartridge holder includes a first latch element located on the insert section. The body includes a second latch element located in the receptacle and protruding inwardly from a side wall section of the receptacle. A radial extension of the first latch element is less than a thickness of the side wall of the insert section or of the
(Continued)

receptacle. A radial protrusion of the second latch element is less than a thickness of the side wall sections of the insert section or of the receptacle.

20 Claims, 3 Drawing Sheets

(51) Int. Cl.
 *A61M 5/20* (2006.01)
 *A61M 5/31* (2006.01)
(52) U.S. Cl.
 CPC .... *A61M 5/31551* (2013.01); *A61M 5/31585* (2013.01); *A61M 5/31535* (2013.01); *A61M 5/31541* (2013.01); *A61M 2005/2492* (2013.01); *A61M 2005/3126* (2013.01); *A61M 2205/581* (2013.01); *A61M 2205/582* (2013.01)
(58) Field of Classification Search
 CPC .......... A61M 5/31541; A61M 5/31535; A61M 2005/2492; A61M 2005/3126; A61M 2205/581; A61M 2205/582
 See application file for complete search history.

(56) References Cited

FOREIGN PATENT DOCUMENTS

| WO | WO 2004/078240 | 9/2004 |
|---|---|---|
| WO | WO 2004/078241 | 9/2004 |
| WO | WO 2008/003560 | 1/2008 |
| WO | WO 2013/153011 | 10/2013 |

OTHER PUBLICATIONS

International Search Report and Written Opinion in International Application No. PCT/EP2017/060508, dated Aug. 17, 2017, 11 pages.

* cited by examiner

HOUSING FOR AN INJECTION DEVICE

CROSS REFERENCE TO RELATED APPLICATIONS

The present application is the national stage entry of International Patent Application No. PCT/EP2017/060508, filed on May 3, 2017, and claims priority to Application No. EP 16168067.3, filed on May 3, 2016, the disclosures of which are incorporated herein by reference.

TECHNICAL FIELD

The present disclosure relates in one aspect to a housing of an injection device, such like a pen-type injector operable for setting and dispensing of a dose of a medicament. In particular, the disclosure relates to an interconnection of two housing components of an injection device

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Document WO 2008/003560 A1 describes for instance a pre-filled injection device having a container and a dose setting mechanism encapsulated inside a housing. The housing is made from two parts which are locked together by a bayonet coupling. In addition to the bayonet coupling, the two parts are also provided with irreversible locking means locking the two parts permanently together.

During a final assembly process of such handheld injection devices a cartridge containing the injectable medicament is positioned and assembled inside a distal housing component forming a cartridge holder. A drive mechanism including at least a piston rod to operably engage with a piston of the cartridge is assembled inside a proximal housing component that forms or constitutes a body. The cartridge holder with the cartridge assembled therein forms a cartridge holder preassembly whereas the body with the drive mechanism assembled therein forms or constitutes a body preassembly.

During a final step of assembly the cartridge holder preassembly and the body preassembly are assembled together. For this a proximal end of the cartridge holder is fixed to a distal end of the body. Typically, cartridge holder and body comprise an insert section and a correspondingly-shaped receptacle so that the proximal end of the cartridge holder and the distal end of the body are assembled in a nested or interleaved way. In a mutually overlapping section there are typically provided positively engaging locking means, such like radially outwardly or radially inwardly extending mutually corresponding snap features. For instance an insert section of the cartridge holder may be provided with at least one or several through holes in a sidewall section that are configured to receive and to engage with at least one radially inwardly protruding latch element provided on an inside facing portion of a sidewall of the receptacle of the body, in which the insert section of the cartridge holder is located.

Such a clip connection based on snap features and holes may be disadvantageous for a barrel of the cartridge made from a vitreous material. Typically, the cartridge firmly attached or assembled inside the cartridge holder may experience a non-neglectable radially inwardly directed compression as the snap features of the receptacle of the body snap into correspondingly-shaped holes in the insert section of the cartridge holder. In order to establish such clip connections the sidewall of interleaved housing sections of cartridge holder and body are temporally subject to at least a marginal radial deformation. Even such marginal or minor radial deformation of the cartridge holder or of its insert section may cause significant stress to the glass cartridge assembled therein.

SUMMARY

The subject matter of the present disclosure can be implemented advantageously in certain embodiments to improve the mechanical connection between housing components of a handheld injection device, such as an injection pen, that provides a reliable and stable fixing of the housing components without exerting significant stress to the glass cartridge during assembly. A mechanical stress level applied to the cartridge should be at least drastically reduced compared to prior art solutions.

In one aspect a housing for an injection device, in particular for a pen-type injection device is provided. The housing comprises a body to accommodate a drive mechanism having at least a piston rod to operably engage with a piston of a cartridge. The cartridge is typically filled with a liquid injectable medicament. The housing further comprises a cartridge holder having a cartridge receiving space to accommodate the cartridge. The cartridge receiving space of the cartridge holder is that interior volume of the cartridge holder that is completely captured or taken by the cartridge when assembled inside the cartridge holder. In a final assembly configuration the cartridge receiving space coincides with the outer circumference and with the outer geometry of the cartridge assembled therein.

The cartridge holder and the body are of substantially tubular shape and extend along an axial direction. The axial direction coincides with the longitudinal axis of the tubular or cylindrically-shaped cartridge holder or with the co-aligned body. The cartridge holder further has an insert section at a proximal end and the body has a receptacle at a distal end to receive the insert section of the cartridge holder. In a final assembly configuration the body and the cartridge holder are aligned substantially parallel with their longitudinal axes and the insert section of the cartridge holder is located and fitted inside the receptacle of the body. Hence, the outer diameter of the insert section matches with the inner diameter of the receptacle. In this way cartridge holder and body are assembled in a nested or interleaved way in which the receptacle and the insert section of body and cartridge holder mutually overlap in a radial direction.

The cartridge holder comprises at least a first latch element located on the insert section. The body comprises at least a second latch element located in the receptacle and protruding radially inwardly from a sidewall section of the receptacle. The first and the second latch elements mutually engage for fixing the cartridge holder to the body and in order to provide a reliable positive engagement of cartridge holder and body. First and second latch elements are configured to form a clip connection or a snap fitting connection of cartridge holder and body. First and second latch elements are therefore configured to provide a positive interlock of cartridge holder and body. Typically but not necessarily first and second latch elements are configured to establish and to provide a non-releasable engagement of cartridge holder and body. Once assembled the first and second latch elements cannot be detached or released without substantially destroying at least one of the cartridge holder and the body. The connection of first and second latch elements is therefore of permanent type or of non-releasable type.

Furthermore, a radial extension or depth of the first latch element is less than a thickness of the sidewall sections of the insert section or of the receptacle. In the same way a radial protrusion of the second latch element is less than a thickness of the sidewall sections of the insert section or of the receptacle. By reducing the radial dimensions of the first latch element and the second latch element a degree of radial deformation of the cartridge holder, in particular of the insert section of the cartridge holder can be reduced compared to solutions known in the prior art. In this way mechanical stress applied to the barrel of the cartridge during a final step of assembly can be remarkably reduced.

In addition to that the first latch element is located at an axial distance from a proximal end of the cartridge receiving space. This axial distance is less than 25% of the axial elongation of the insert section. In effect and by arranging the first latch element to or near the proximal end of the cartridge holder a degree and magnitude of radial deformation of the cartridge holder can be further reduced at least in regions that are located at a larger distance from the proximal end of the cartridge holder or from the proximal end of the cartridge receiving space. The axial positioning of the first latch element with regard to the proximal end of the cartridge receiving space and also with regard to the proximal end of the insert section in combination with the radial extension or depth of the first latch element and/or in combination with the radial extension of the second latch element provides a rather small degree or small extent of radial deformation of the cartridge holder. In effect, mechanical stress to the vitreous barrel of the cartridge can be reduced and a likelihood of fracture or damaging of the cartridge during and due to the mutual assembly of body and cartridge holder can be reduced.

According to another embodiment the axial distance between the first latch element and the proximal end of the cartridge receiving space is less than 20%, less than 15%, less than 10% or less than 5% of the elongation of the insert section. Typically the first latch element is positioned in the axial direction rather close to the proximal end of the cartridge receiving space of the cartridge holder. It is located rather close to the proximal end of the cartridge when assembled inside the cartridge holder.

In typical implementation the piston sealing the proximal end of the cartridge is located rather close to the proximal end of the cartridge. The piston therefore provides a further mechanical stabilizing effect to the cartridge, in particular to the barrel of the cartridge. Since the piston is located inside the tubular-shaped barrel of the cartridge the cartridge is becomes less sensitive with regard to radially inwardly directed compressive forces in the region of the piston compared to other axial regions where the liquid medicament is located. By arranging the first latch element rather close to the proximal end of the cartridge receiving space the mutually corresponding first and second latch elements of cartridge holder and body will be located in a well-defined axial region, e.g. coinciding with the axial elongation of the piston of the cartridge when the cartridge is assembled inside the cartridge holder and hence inside the injection device.

In addition to that a vitreous barrel of a cartridge typically comprises a bulged rim at its proximal end. Such a bulged rim or bulged portion is due to the manufacturing process of the glass barrel. It can be considered as an enamel edge. Such a bulged portion at a proximal end may inherently provide a structural reinforcement of the barrel. So at the very proximal end the vitreous barrel of the cartridge is inherently mechanically stabilized and may easily withstand radially inwardly directed compressive forces during the mutual assembly of cartridge holder and body of the injection device.

It is hence of particular benefit to arrange the first and second mutually engaging latch elements of cartridge holder and body in an axial region that substantially overlaps with the proximal end of the vitreous barrel of the cartridge.

According to another embodiment the first latch element is located at a distal offset from the proximal end of the cartridge receiving space. In such a configuration the first latch element as well as the second latch element are located distally from the proximal end of the cartridge barrel. Typically and since the axial offset from the proximal end of the cartridge receiving space is less than 25% of the total axial elongation of the insert section the first and the second latch elements will be located in an axial region that coincides or overlaps with the piston of the cartridge. In such an axial position the cartridge is inherently mechanically stabilized through the piston located in its interior and sealing the interior volume of the cartridge in proximal direction.

According to another embodiment the first latch element is located at a proximal offset from the proximal end of the cartridge receiving space. Here, the proximal end of the cartridge holder may protrude proximally from the proximal end of the barrel of the cartridge. Such a configuration might be beneficial in that a magnitude of radial deformation in the region of the first latch element is transferred to a smaller degree or to a smaller extent into an axial region of the sidewall of the cartridge holder that overlaps or coincides with the axial position of the cartridge assembled inside the cartridge holder.

Here, a kind of leverage effect can be utilized. A radially inwardly directed deformation of e.g. a proximal end of the cartridge holder will have the largest magnitude just in an axial position where the first latch element is located. With an increasing axial distance from the first latch element, e.g. toward the distal end of the cartridge holder the magnitude of radial deformation will become gradually smaller. With the first latch element axially protruding from the proximal end of the cartridge receiving space and hence axially protruding from the proximal end of the cartridge a rather large degree or magnitude of radial deformation of the insert section and hence of the cartridge holder will have a smaller impact in a region of the sidewall of the cartridge holder that is located at a given axial distance from the first latch element. In this way, radial load or radial stress applied to the vitreous barrel of the cartridge during a final step of assembly can be further reduced.

According to another embodiment an inside facing portion of the insert section is tapered towards the proximal end. Here, the proximal end of the insert section comprises a tapered section. In other words, the radial thickness of the sidewall of the insert section of the cartridge holder constantly or gradually decreases towards the proximal end of the insert section. Typically, it is only the inside facing portion of the sidewall of the insert section that is tapered. In this way a radial gap size between an inside facing sidewall section of the insert section of the cartridge holder and an outer circumferential surface of the cartridge assembled inside the cartridge holder can be substantially increased. Due to the tapered section of the insert section the free space between the cartridge and the cartridge holder can be increased at least in an axial region where the first latch element is located. In this way a degree or magnitude of radial deformation of the insert section of the cartridge holder can be increased without a substantial impact on the vitreous barrel of the cartridge assembled therein.

In another embodiment a tapered angle of the tapered section is larger than 1° or larger than 2° with regard to the axial direction. So as seen in a longitudinal cross-section the proximal end of the insert section, typically that portion of the insert section that is located proximal from the first latch element, comprises a wedge-like shape with a constantly decreasing sidewall thickness towards the proximal end. Typically, the taper angle of the tapered section is less than 10°, less than 5° or less than 3° with regard to the axial direction. First implementations have shown, that already a rather small tapered angle in the region of 2° or 3° provides a substantial improvement for reducing radial stress to the vitreous barrel during the final assembly process of the housing of the injection device.

In another embodiment the receptacle comprises at least one of a longitudinal groove and a longitudinal projection to engage with at least one of a correspondingly-shaped longitudinal projection and a longitudinal groove of the insert section. The longitudinal grooves and projections extend towards the proximal end of the insert section and to the distal end of the receptacle of the body. The longitudinal grooves and projections provide a rotation invariant coupling of the body and the cartridge holder. In addition to that the mutually corresponding and inter-engaging longitudinal grooves and projections define an angular orientation or angular position of the cartridge holder relative to the body in order to enable a smooth insertion of the insert section into the receptacle.

The longitudinal groove and the longitudinal projection further enable a smooth running sliding displacement during the assembly of cartridge holder and body. During the mutual assembly of the housing components, namely of cartridge holder and body, the at least one longitudinal projection slides along the longitudinal groove. By means of mutually corresponding and inter-engaging projections and grooves on the outside facing sidewall portion of the insert section and on the inside facing sidewall section of the receptacle a well-defined axial sliding displacement of cartridge holder and body is provided.

In another embodiment the first latch element is located on the longitudinal projection and the second latch element is located in the longitudinal groove. Alternatively, the first latch element is located in the longitudinal groove whereas the second latch element is located on the longitudinal projection. When having several first and second latch elements and several longitudinal grooves and longitudinal projections, e.g. equidistantly distributed along the outer circumference of the insert section and the inner circumference of the receptacle, it is also conceivable, that the insert section comprises both, at least one longitudinal projection and at least one longitudinal groove to mate with and to engage with at least one longitudinal groove and at least one longitudinal projection on the inside-facing sidewall portion of the receptacle of the body.

By having the first latch element located on one of the longitudinal projections and the longitudinal groove and by having the second latch element located on one of the longitudinal groove and the longitudinal projection a well-defined mutual engagement of first and second latch elements can be provided when the longitudinal groove slides along the longitudinal projection during the assembly process and during insertion of the insert section into the receptacle.

In still another embodiment the first latch element comprises a recess in the sidewall of the insert section. The radial depth of the recess is substantially smaller than the thickness of the sidewall of the insert section. In typical embodiments the radial depth of the first latch element is less than 60%, less than 50%, less than 40% or even less than or equal to 30% of the radial thickness of the sidewall of the insert section. By reducing the radial depth or the radial extension of the first latch element the total magnitude of radial deformation of the insert section can be decreased during insertion into the receptacle of the body.

According to another embodiment the radial extension of the second latch element is less than 60%, less than 50%, less than 40% or less than or equal to 30% of the radial thickness of the sidewall of the receptacle or of the sidewall of the insert section. In this way the degree and magnitude of radial deformation of the insert section can be further reduced. This may be further beneficial to reduce mechanical stress applied to the vitreous barrel of the cartridge during a final process of assembly of housing components.

In still another embodiment the first latch element comprises an abutment facing in distal direction to engage with an abutment of the second latch element facing in proximal direction. Typically, first and second latch elements are of double hook configuration. When in mutual engagement the abutments of first and second latch elements are in axial abutment and therefore provide a well-defined axial pull apart threshold that is above a desired mechanical strength of the joint or of the interface of cartridge holder and body.

It is of particular benefit when the abutment of the first latch element and the abutment of the second latch element have a radial extension that is substantially less than 60%, less than 50%, less than 40% or equal to or less than 30% of the thickness of a respective sidewall. In this way a double hook joint of first and second latch elements can be established that provides a rather high axial pull apart force and pull apart strength in combination with a comparatively small degree or magnitude of radial deformation during assembly of body and cartridge holder. In addition to that and by reducing the radial extension of the first and second latch elements the structural integrity and structural stability of insert section and receptacle can be enhanced. Making use of a through opening in a sidewall section of body or cartridge holder always comes along with a structural weakening. By avoiding any through openings in the sidewall of body and cartridge holder at least in the regions of the insert section and the receptacle a rather stable and robust positively engaging joint of body and cartridge holder can be established.

According to another embodiment the second latch element comprises a wedge-shaped ramp section protruding radially inwardly from the sidewall of the receptacle. A wedge-shaped ramp section provides a rather smooth radial deformation of the receptacle and/or of the insert section of the cartridge holder during the process of mutual assembly of body and cartridge holder. In addition to that an axial assembly force for establishing a positive interlock or a positively engaging interconnection of body and cartridge holder can be lowered, thus allowing for an easy and smooth assembly process of cartridge holder and body.

In addition to that also the first latch element may comprise a correspondingly-shaped recess or recessed portion in the sidewall of the insert section to receive and to engage with the wedge-shaped ramp section of the second latch element provided on the inside-facing sidewall of the receptacle of the body. In this way a rather firm and stable mutual interconnection of cartridge holder and body can be provided.

In another embodiment the abutment of the second latch element confines the ramp section of the second latch element. While the ramp section extends at a certain angle towards the interior of the receptacle and while the ramp section gradually protrudes from the inside of the sidewall of the receptacle towards the proximal direction the abutment finally terminates the ramp section and extends radially outwardly so that the abutment faces in proximal direction. A radial outer end of the abutment then coincides with the inside face of the sidewall of the receptacle.

According to another aspect there is also provided an injection device for administering an injectable medicament into biological tissue. The injection device, which is typically configured as a handheld injection device such as an injection pen comprises a housing as described above. The injection device further comprises a drive mechanism assembled inside the body of the housing and further comprises a cartridge that is assembled inside the cartridge holder. Typically, the injection device is configured as a pre-filled injection device or as a disposable injection device with the cartridge radially assembled therein. The injection device may be configured for a one-time use or for several consecutive usages.

After the content of the cartridge has been used up the entire device may be intended to be discarded in its entirety. Hence, the drive mechanism is not configured for a reset operation nor is the cartridge intended to be replaced by a new one. When configured and designed as a disposable or prefilled injection device the positively engaging first and second latch elements of the body and of the cartridge holder are configured to be of permanent and non-releasable type.

Once the first and second latch elements positively engage there is no way of disengaging the same except when destroying one of the housing components' body or cartridge holder.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made without departing from the spirit and scope of the invention. Further, it is to be noted, that any reference numerals used in the appended claims are not to be construed as limiting the scope of the invention.

BRIEF DESCRIPTION OF THE FIGURES

In the following, an embodiment is described in detail by making reference to the drawings, in which.

DETAILED DESCRIPTION

Figure 1:
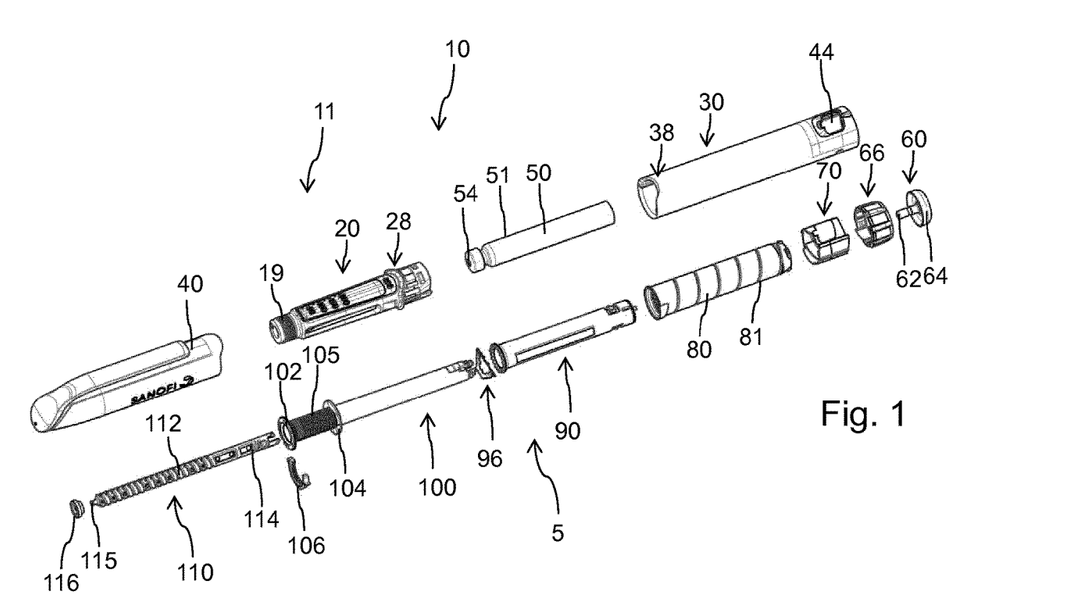
FIG. 1 is an exploded view of the various components of the injection device.
Figure 2:
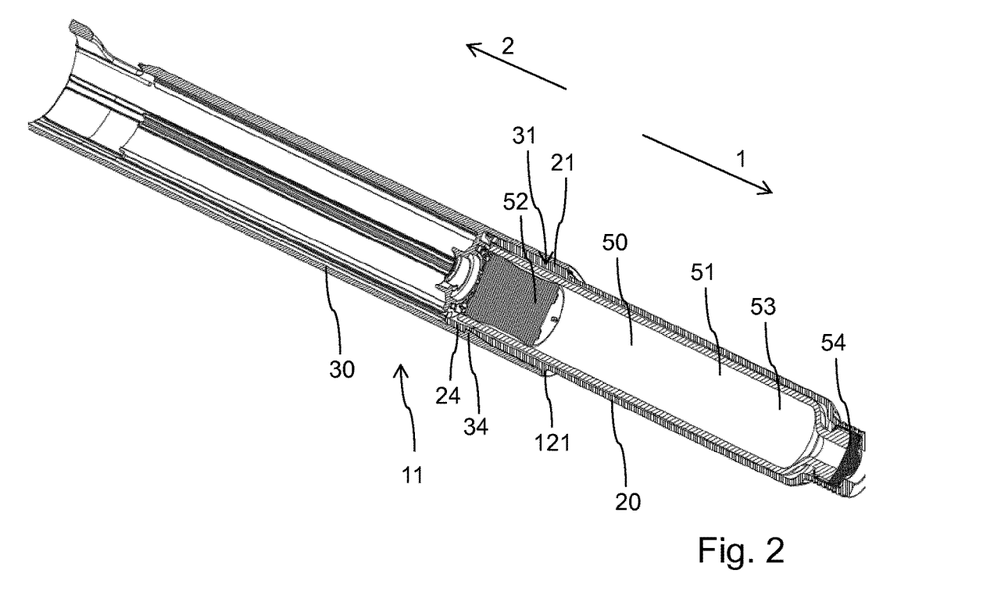
FIG. 2 is a longitudinal cross-section through the housing of the injection device with the cartridge assembled inside the cartridge holder.

The injection device 10 as shown in FIGS. 1 and 2 is configured as a pen-type injector. It comprises an elongated housing 11 extending in a longitudinal or axial direction. Towards a distal direction 1 the injection device 10 comprises a distal housing component denoted as cartridge holder 20. In the opposite longitudinal direction the housing 11 comprises a second housing component denoted as body 30. Both housing components, namely cartridge holder 20 and body 30 are of tubular and elongated shape. The cartridge holder 20 is configured to accommodate a cartridge 50 comprising a tubular-shaped barrel 51 and being filled with a liquid medicament 53. At a distal end the cartridge 50 comprises a pierceable seal 54 typically comprising a pierceable septum of an elastomeric material.

At the opposite proximal end the cartridge 50 is sealed by a piston 52 slidably arranged inside the barrel 51 of the cartridge 50. For dispensing of a dose of the liquid medicament 53 the cartridge holder 20 comprises a threaded socket 19 at its distal end to receive a correspondingly threaded needle assembly with a double-tipped injection needle. A proximal tipped end of the injection needle of the needle assembly, which is presently not illustrated, is configured to pierce the distal seal 54 of the cartridge 50 thereby gaining access to the interior of the cartridge 50. The distal end of the injection needle is then configured to puncture biological tissue to deliver the medicament. For medicament delivery the piston 52 is to be displaced in distal direction 1 under the action of a distally advancing piston rod 110 of a drive mechanism 5 of the injection device 10. The drive mechanism 5 is accommodated and fixed in the body 30 of the injection device 10. There is further provided a protective cap 40 covering the distal portion of the cartridge holder 20 when assembled thereto.

The cartridge holder 20 and the body 30 are to be interconnected by means of a positive connection as it is explicitly shown in FIG. 2. The cartridge holder 20 comprises a proximal connecting end to irreleasably interconnect with a distal connecting end of the body 30. The cartridge holder 20 and the body 30 are interconnectable in an interleaved or nested way. In the presently illustrated embodiment the proximal connecting end of the cartridge holder 20 comprises an insert section 21 axially confined in distal direction 1 by a radially outwardly extending annular ridge 121. The distal connecting end of the body 30 comprises a receptacle 31 to axially receive the insert section 21 of the cartridge holder 20. The outer diameter of the insert section 21 exactly matches with the inner diameter of the receptacle 31 so that the insert section 21 can be inserted into the receptacle 31 by means of a sliding motion in proximal direction 2 relative to the body 30.

Figures 3, 4:
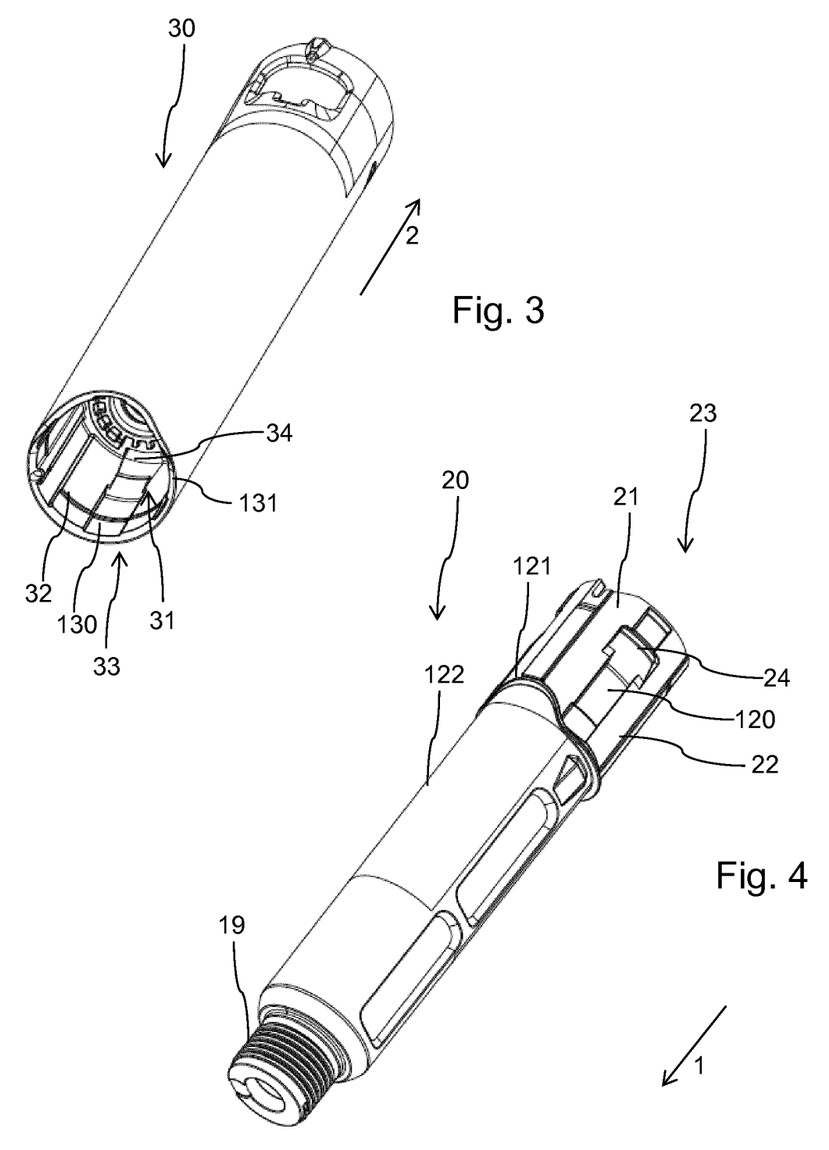
FIG. 3 is a perspective illustration of the body of the injection device.
FIG. 4 is a perspective view of the cartridge holder.

From the combination of the FIGS. 2-4 it is immediately apparent, that the insert section 21 of the cartridge holder 20 is located at a proximal end 23 of the cartridge holder 20 and that the receptacle 31 is located at a distal end 33 of the body 30. Once mutually assembled the insert section 21 of the cartridge holder 20 is fully or entirely located inside the receptacle 31 of the body 30. The insert section 21 is confined and delimited in distal direction by an annular ridge 121 protruding radially outwardly from an outer surface 122 of the cartridge holder 20. When in a final assembly configuration a proximal-facing edge of the annular ridge 121 is in axial abutment with a distal face 131 of the sidewall 32 of the body 30.

As it is apparent from FIGS. 3 and 4, the inside-facing sidewall 32 of the receptacle 31 comprises at least one or several longitudinal grooves 130 to receive a correspondingly-shaped radially outwardly extending longitudinal projection 130 on the sidewall 22 of the insert section 21 of the cartridge holder 20. The projection 120 as well as the groove 130 extend to the proximal end 23 of the cartridge holder 20 and to the distal end 33 of the body 30, respectively. As it is apparent from FIG. 5 there are provided several longitudinal projections 120 on the outer circumference of the insert section 21. There are further provided correspondingly-shaped longitudinal grooves 130 on the inside of the sidewall 32 of the receptacle 31. The longitudinal projections 120 received in the longitudinal grooves 130 provide a rotation inhibiting fastening and a respective sliding motion of the insert section 21 into the receptacle 31.

Figure 5:
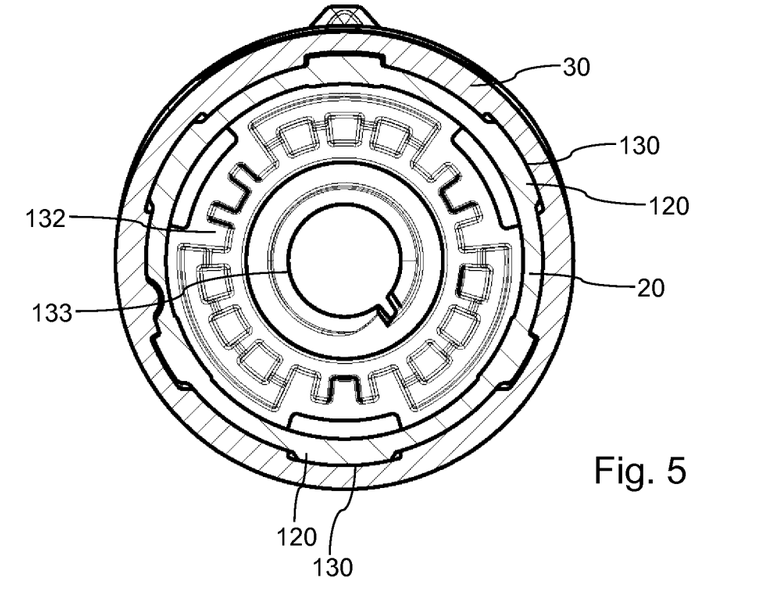
FIG. 5 is a cross-section through the interface of cartridge holder and body in the region of receptacle and insert portion.

The sliding axial insertion motion of the insert section 21 into the receptacle 31 is delimited as the annular ridge 121 axially abuts with the distal face 131 of the sidewall 32 of the body 30.

Figure 6:
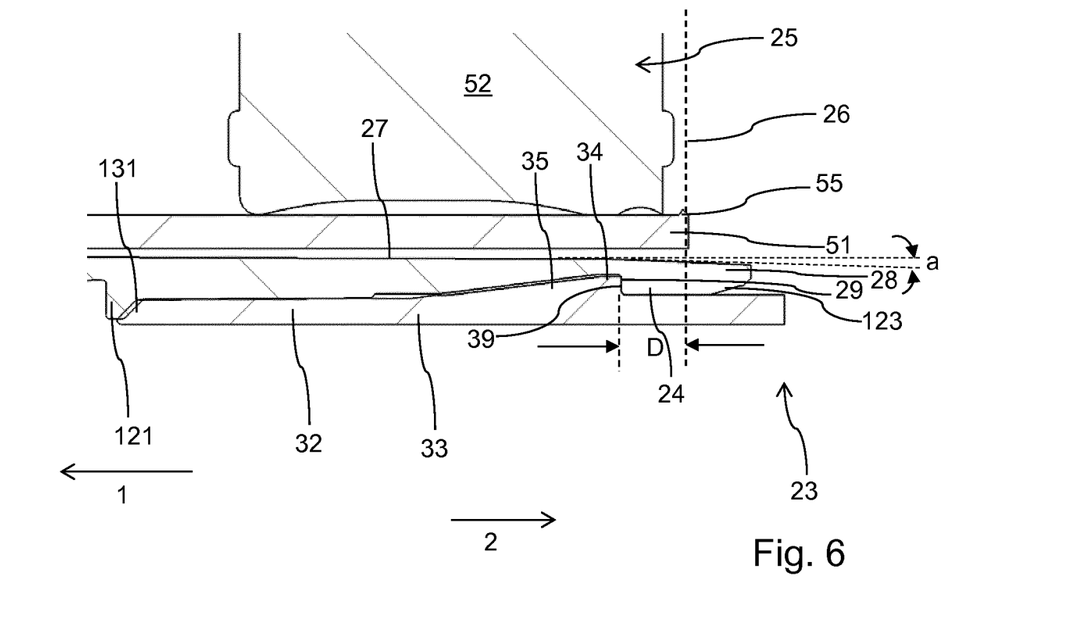
FIG. 6 is an enlarged view of a section of FIG. 2 in the region of the receptacle and the insert section of body and cartridge holder.

In addition to the longitudinal projections 120 and the longitudinal grooves 130 the interface of insert section 21 and receptacle 31 is further provided with first and second latch elements 24, 34 as shown in the cross-section according to FIG. 6. Here, the mutual engagement of first and second latch elements 24, 34 provides a kind of a double hooked latch mechanism. First and second latch elements 24, 34 are correspondingly-shaped. In the presently illustrated embodiment the first latch element 24 comprises a recessed structure that is terminated or delimited in proximal direction 2 by a distally-facing abutment 29 extending radially outwardly from the bottom of the recessed structure.

Correspondingly to the first latch element 24 the second latch element 34 provided at the inside of the sidewall 32 of the receptacle 31 comprises a ramp section 35 that is delimited or confined in proximal direction 2 by a proximally-facing abutment 39. When a final assembly configuration has been reached as it is shown in FIG. 6 the mutually corresponding abutments 29, 39 axially engage and provide an axial non-releasable fixing of cartridge holder 20 and body 30.

As it is further shown in FIG. 6 the radial extension or radial depth of the first latch element 24 and of the second latch element 34, in particular the radial extension of the mutually engaging abutments 29, 39 of first and second latch elements 24, 34 is less than the thickness of the sidewalls 22, 32 of the cartridge holder 20 or of the body 30, respectively. Reducing the radial extension of first and second latch elements 24, 34 to less than 60%, less than 50%, less than 40% or less than 30% of the thickness of the respective sidewall 22, 32 is rather beneficial in that a degree or magnitude of inevitable radial deformation of the insert section 21 can be reduced to a minimum during the insertion into the receptacle and during establishing of the snap fit connection as shown in FIG. 6.

In addition to that it is of particular benefit, that the axial position of the mutually engaging first and second latch elements 24, 34 is within a predefined axial distance D with regard to the proximal end 26 of a cartridge receiving space 25 of the cartridge holder 20. The cartridge receiving space 25 is the imaginary space of the cartridge holder 20 in which the cartridge 50 is located when assembled inside the cartridge holder 20. Typically, the outer geometry of the cartridge 50 exactly matches with the imaginary cartridge receiving space 25. The proximal end 26 of the cartridge receiving space 25 as indicated in FIG. 6 coincides with the proximal end of the cartridge 50 when assembled inside the cartridge holder 20.

In various embodiments the axial distance D between the proximal end 26 of the cartridge receiving space 25 and the latch elements 24, 34, in particular the abutments 29, 39 of the first and second latch elements 24, 34 is less than 25% of the axial elongation of the insert section 21. The axial elongation of the insert section 21 is given by the axial distance between the annular ridge 121 and the proximal end 23 of the cartridge holder 20. In embodiments where the annular ridge 121 has wavelike-shaped undulation extending in axial direction the axial elongation of the insert section is determined as the axial distance between the median axial position of the annular ridge 121 and the median axial position of the proximal end of the cartridge holder 20 as seen in tangential or circumferential direction.

Given in total dimensions the axial position of the mutually engaging first and second latch elements is axially offset from the proximal end of the cartridge by not more than 2.5 mm.

In the illustration according to FIG. 6 the axial distance D from the proximal end 26 of the cartridge receiving space 25 and the first latch element 24 is about 11% of the total axial elongation of the insert section 21. In the illustrated embodiment the first latch element 24, hence its abutment 29 is located distally from the proximal end 26 of the cartridge receiving space 25 and hence distally from the proximal end of the barrel 51 of the cartridge 50. Other configurations are likewise conceivable wherein the first latch element 24 and hence the abutment 29 is located proximally from the proximal end 26 of the cartridge receiving space 25 and hence proximally from the proximal end of the barrel 51 of the cartridge 50.

The specific axial position of the latch element 24 as well as of the correspondingly-shaped and correspondingly-positioned latch element 34 is selected such that a radial contact between the inside of the sidewall 22 of the cartridge holder 20 and the outside of the barrel 51 of the cartridge 50 only takes place in the region of the barrel 51 of the cartridge 50 where the piston 52 of the cartridge 50 is located. The piston 52 provides a mechanical stabilization and a kind of a counterforce against radially inwardly directed pressure or stress applied from outside the cartridge 50 to the sidewall 51 of the cartridge 50.

In situations where the latch element 24 and hence the latch element 34 are located proximally from the proximal end of the barrel 51 of the cartridge 50, the effect of a radially directed deformation of the sidewall 22 of the cartridge holder 20 can even be dampened. A radially inwardly directed deformation of the proximal end of the sidewall 22 of the cartridge holder 20 during assembly into the receptacle 31 of the body is typically governed by the geometry and location of the mutually corresponding latch elements 24, 34. With the latch elements 24, 34 being located axially offset and proximally offset from the proximal end of the barrel 51 of the cartridge a radial deformation will be less prominent and of smaller magnitude in the region of the barrel 51 of the cartridge 50.

Furthermore and as illustrated in FIG. 6, the insert section 21 comprises a tapered section 28 at its proximal end 23. The tapered section 28 is characterized by a taper angle a defining a rather slanted shape of the inside section of the sidewall 22 of the insert section 21 of the cartridge holder 20. The taper angle a may be as small as 1° or 2° or 3° compared to the axial elongation of the cartridge holder 20. The tapered section 28 is only provided at the inside of the sidewall 22 of the insert section 21. In this way a radial gap size between the sidewall 22 of the insert section 21 and an outside surface of the barrel 51 of the cartridge 50 can be increased at least in that region where the first and second latch elements 24, 34 are located upon reaching the final assembly configuration as shown in FIG. 6. Increasing of a radial gap size between the inside 27 of the sidewall 22 of the insert section 21 and the outside of the barrel 51 of the cartridge 50 also decreases mechanical stress to the vitreous barrel 51 of the cartridge 50 during the final step of assembly.

Further shown in FIG. 6 is that the proximal end of the barrel 51 of the cartridge 50 comprises a bulged portion 55 that arises from the manufacturing process of the glass cartridge 50. It is of particular benefit, when the latch elements 24, 34 are located rather close to the bulged portion 55 of the barrel 51 since the radially thickened bulged portion 55 inherently provides a portion of increased stability and mechanical strength of the cartridge 50 that may easily tolerate radially inwardly directed mechanical load or stress during the mutual assembly of cartridge holder 20 and receptacle 30.

As it is further illustrated in FIG. 6 the radially inwardly protruding second latch element 34 comprises a ramp section 35 that allows and enables a rather smooth running engagement of first and second latch elements 24, 34 as the insert section 21 is inserted into the receptacle in axial direction. As can be seen further from FIG. 6 the insert section 21 comprises a beveled edge 123 on the outer circumference of the proximal end 23 of the sidewall 22. This beveled edge 123 facilitates insertion of the proximal end 23 of the cartridge holder 20 into the receptacle 31 of the body 30.

The drive mechanism 5 comprises numerous mechanically interacting components. A flange like support 132 of the body 30 comprises a threaded axial through opening 133 threadedly engaged with a distal thread 112 of the piston rod 110. The distal end of the piston rod 110 comprises a bearing 115 on which a pressure foot 116 is free to rotate with the longitudinal axis of the piston rod 110 as an axis of rotation. The pressure foot 116 is configured to axially abut against the proximally facing thrust receiving surface of the piston 52 of the cartridge 50. During a dispensing action the piston rod 110 rotates relative to the body 30 thereby experiencing a distally directed advancing motion relative to the body 30 and hence relative to the barrel 51 of the cartridge 50. As a consequence, the piston 52 of the cartridge 50 is displaced in distal direction by a well-defined distance due to the threaded engagement of the piston rod 110 with the body 30.

The piston rod 110 is further provided with a second thread 114 at its proximal end. The distal thread 112 and the proximal thread 114 are oppositely handed.

There is further provided a drive sleeve 100 having a hollow interior to receive the piston rod 20. The drive sleeve 100 comprises an inner thread threadedly engaged with the proximal thread 114 of the piston rod 110. Moreover, the drive sleeve 100 comprises an outer threaded section 105 at its distal end. The threaded section is axially confined between a distal flange portion 102 and another flange portion 104 located at a predefined axial distance from the distal flange portion 102. Between the two flange portions 102, 104 there is provided a last dose limiting member 106 in form of a semi-circular nut having an internal thread matching the threaded section 105 of the drive sleeve 100.

The last dose limiting member 106 further comprises a radial recess or protrusion at its outer circumference to engage with a complementary-shaped recess or protrusion at an inside of the sidewall 32 of the body 30. In this way the last dose limiting member 106 is splined to the body 30. A rotation of the drive sleeve 100 in a dose incrementing or clockwise direction during consecutive dose setting procedures leads to an accumulative axial displacement of the last dose limiting member 106 relative to the drive sleeve 100. There is further provided an annular spring 96 that is in axial abutment with a proximally facing surface of the flange portion 104. Moreover, there is provided a tubular-shaped clutch member 90. At a first end the clutch member 90 is provided with a series of circumferentially directed saw teeth. Towards a second opposite end of the clutch member 90 there is located a radially inwardly directed flange.

Furthermore, there is provided a dose dial or dose indicating sleeve 80. The dose indicating sleeve 80 is provided outside of the spring 96 and the clutch member 90 and is located radially inward of the body 30. A helical groove 81 is provided about an outer surface of the dose indicating sleeve 80. The body 30 is provided with a window 44 through which a part of the outer surface of the dose indicating sleeve 80 can be seen. The body 30 is further provided with a helical rib at an inside sidewall portion of an insert piece 70, which helical rib is to be seated in the helical groove 81 of the dose indicating sleeve 80. The tubular shaped insert piece 70 is inserted into the proximal end of the body 30. It is rotationally and axially fixed to the body 30. There are provided first and second stops on the body 30 to limit a dose setting procedure during which the dose indicating sleeve 80 is rotated in a helical motion relative to the body 30.

A dose dial grip 66 is disposed about an outer surface of the proximal end of the dose indicating sleeve 80. An outer diameter of the dose dial 66 typically corresponds to the outer diameter of the body 30. The dose dial 66 is secured to the dose indicating sleeve 80 to prevent relative movement therebetween. The dose dial 66 is provided with a central opening.

Furthermore, a dose button 60 of generally T-shape is provided at a proximal end of the injection device 10. A stem 62 of the dose button 60 extends through the opening in the dose dial 66 through an inner diameter of extensions of the drive sleeve 100 and into a receiving recess at the proximal end of the piston rod 110. The stem 62 is retained for limited axial movement in the drive sleeve 100 and against rotation with respect thereto. A head 64 of the dose button 60 is generally circular. A skirt extends from a periphery of the head 64 and is further adapted to be seated in a proximally accessible annular recess of the dose dial 66.

To dial a dose a user rotates the dose dial 66. With the spring 96 also acting as a clicker and the clutch member 90 engaged, the drive sleeve 100 the spring or clicker 96, the clutch member 90 and the dose indicating sleeve 80 rotate with the dose dial 66. Audible and tactile feedback of the dose being dialed is provided by the spring 96 and by the clutch member 90. Torque is transmitted through saw teeth between the spring 96 and the clutch member 90. The helical groove 81 on the dose indicating sleeve 80 and a helical groove in the drive sleeve 100 have the same lead. This allows the dose indicating sleeve 80 to extend from the body 30 and the drive sleeve 100 to climb the piston rod 110 at the same rate. At a limit of travel a radial stop on the dose indicating sleeve 80 engages either with a first stop or a second stop provided on the body 30 to prevent further movement. Rotation of the piston rod 110 is prevented due to the opposing directions of the overall and driven threads on the piston rod 110.

The last dose limiting member 106 keyed to the body 30 is advanced along the threaded section 105 by the rotation of the drive sleeve 100. When a final dose dispensed position is reached, a radial stop formed on a surface of the last dose limiting member 106 abuts a radial stop on the flange portion 104 of the drive sleeve 100, preventing both, the last dose limiting member 106 and the drive sleeve 100 from rotating further.

Should a user inadvertently dial beyond the desired dosage, the pen-injector 10 allows the dosage to be dialed down without dispense of the medicament from the cartridge 50. For this the dose dial 66 is simply counter-rotated. This causes the system to act in reverse. A flexible arm of the spring or clicker 96 then acts as a ratchet preventing the spring 96 from rotating. The torque transmitted through the clutch member 90 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the dose button 60. This displaces the clutch member 90 axially with respect to the dose indicating sleeve 80 causing dog teeth thereof to disengage. However, the clutch member 90 remains keyed in rotation to the drive sleeve 100. The dose indicating sleeve 80 and the dose dial 66 are now free to rotate in accordance with the helical groove 81.

The axial movement deforms the flexible arm of the spring 96 to ensure the saw teeth cannot be overhauled during dispense. This prevents the drive sleeve 100 from rotating with respect to the body 30 though it is still free to move axially with respect thereto. The deformation is subsequently used to urge the spring 96 and the clutch member 90 back along the drive sleeve 100 to restore the connection between the clutch member 90 and the dose indicating sleeve 80 when the distally directed dispensing pressure is removed from the dose button 60.

The longitudinal axial movement of the drive sleeve 100 causes the piston rod 110 to rotate through the through opening 133 of the support 132 of the body 30, thereby to advance the piston 52 in the cartridge 50. Once the dialed dose has been dispensed, the dose indicating sleeve 80 is prevented from further rotation by contact of a plurality of members extending from the dose dial 66 with a corresponding plurality of stops. A zero dose position is finally determined by the abutment of one of axially extending edges of members of the dose indicating sleeve 80 with a corresponding stop of the body 30.

The drive mechanism 5 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference. Hence, the interface and interconnection of housing components, such like the cartridge holder 20 and the body 30 as explained above can be generally implemented with a large variety of different drive mechanisms.

REFERENCE NUMBERS 1 distal direction
2 proximal direction
5 drive mechanism
10 injection device
11 housing
19 threaded socket
20 cartridge holder
21 insert section
22 sidewall
23 proximal end
24 latch element
25 cartridge receiving space
26 proximal end
27 inside
28 tapered section
29 abutment
30 body
31 receptacle
32 sidewall
33 distal end
34 latch element
35 ramp section
39 abutment
40 cap
44 window
50 cartridge
51 barrel
52 piston
53 medicament
54 seal
60 dose button
62 stem
64 head
66 dose dial
70 insert piece
80 dose indicating sleeve
81 helical groove
90 clutch member
96 spring
100 drive sleeve
102 distal flange portion
104 flange portion
105 threaded section
106 last dose limiting member
110 piston rod
112 distal thread
114 proximal thread
115 bearing
116 pressure foot
120 longitudinal projection 121 annular ridge
122 outer surface
123 beveled edge
130 longitudinal groove
131 distal face
132 support
133 through opening

The invention claimed is:

1. A housing for an injection device, the housing comprising:
- a cartridge holder comprising a cartridge receiving space to accommodate a cartridge filled with a liquid injectable medicament, the cartridge holder being of substantially tubular shape and extending in an axial direction, the cartridge holder comprising an insert section at a proximal end of the cartridge holder, the cartridge holder comprising a first latch element located on the insert section of the cartridge holder; and
- a body to accommodate a drive mechanism comprising a piston rod to operably engage with a piston of the cartridge, the body being of substantially tubular shape and extending in the axial direction, the body comprising a receptacle at a distal end of the body, the body comprising a second latch element located in the receptacle of the body, the second latch element protruding radially inward from a side wall section of the receptacle, wherein the receptacle is configured to receive the insert section of the cartridge holder;
- wherein the first latch element and the second latch element are mutually engageable for fixing the cartridge holder to the body;
- wherein a radial extension of the first latch element of the cartridge holder is less than a thickness of a side wall of the insert section or the side wall section of the receptacle,
- wherein a radial protrusion of the second latch element of the body is less than a thickness of the side wall of the insert section or the side wall section of the receptacle,
- wherein the first latch element is located at an axial distance from a proximal end of the cartridge receiving space that is less than 25% of an axial elongation of the insert section, and
- wherein an inside surface of the side wall of the insert section is tapered towards the proximal end of the cartridge holder and comprises a tapered section.

2. The housing according to claim 1, wherein the axial distance between the first latch element and the proximal end of the cartridge receiving space is less than 15% of the axial elongation of the insert section.

3. The housing according to claim 2, wherein the axial distance between the first latch element and the proximal end of the cartridge receiving space is less than 5% of the axial elongation of the insert section.

4. The housing according to claim 1, wherein the first latch element is located at a distal offset from the proximal end of the cartridge receiving space.

5. The housing according to claim 1, wherein the first latch element is located at a proximal offset from the proximal end of the cartridge receiving space.

6. The housing according to claim 1, wherein a taper angle of the tapered section is larger than 1° with regard to the axial direction.

7. The housing according to claim 1, wherein a taper angle of the tapered section is larger than 0° and smaller than 10° with regard to the axial direction.

8. The housing according to claim 7, wherein the taper angle of the tapered section is smaller than 5° with regard to the axial direction.

9. The housing according to claim 1, wherein the receptacle comprises a longitudinal groove to engage with a correspondingly shaped longitudinal projection of the insert section.

10. The housing according to claim 9, wherein the first latch element is located on the longitudinal projection, and the second latch element is located in the longitudinal groove.

11. The housing according to claim 1, wherein the receptacle comprises a longitudinal projection to engage with a correspondingly shaped longitudinal groove of the insert section.

12. The housing according to claim 1, wherein the first latch element comprises a recess in the side wall of the insert section.

13. The housing according to claim 1, wherein the radial protrusion of the second latch element is less than or equal to 60% of the thickness of the side wall section of the receptacle.

14. The housing according to claim 13, wherein the radial protrusion of the second latch element is less than or equal to 40% of the thickness of the side wall section of the receptacle.

15. The housing according to claim 1, wherein the first latch element comprises an abutment facing in a distal direction to engage with an abutment of the second latch element facing in a proximal direction.

16. The housing according to claim 1, wherein the second latch element comprises a wedge shaped ramp section protruding radially inward from the side wall section of the receptacle.

17. The housing according to claim 16, wherein an abutment of the second latch element is configured to confine the wedge shaped ramp section.

18. An injection device for administering an injectable medicament into biological tissue, the injection device comprising:
- a housing comprising:
  - a cartridge holder comprising a cartridge receiving space to accommodate a cartridge filled with a liquid injectable medicament, the cartridge holder being of substantially tubular shape and extending in an axial direction, the cartridge holder comprising an insert section at a proximal end of the cartridge holder, the cartridge holder comprising a first latch element located on the insert section of the cartridge holder; and
  - a body to accommodate a drive mechanism comprising a piston rod to operably engage with a piston of the cartridge, the body being of substantially tubular shape and extending in the axial direction, the body comprising a receptacle at a distal end of the body, the body comprising a second latch element located in the receptacle of the body, the second latch element protruding radially inward from a side wall section of the receptacle, wherein the receptacle is configured to receive the insert section of the cartridge holder;
  - wherein the first latch element and the second latch element are mutually engageable for fixing the cartridge holder to the body, wherein a radial extension of the first latch element of the cartridge holder is less than a thickness of a side wall of the insert section or the side wall section of the receptacle, wherein a radial protrusion of the second latch element of the body is less than a thickness of the side wall of the insert section or the side wall section of the receptacle, wherein the first latch element is located at an axial distance from a proximal end of the cartridge receiving space that is less than 25% of an axial elongation of the insert section and wherein an inside surface of the side wall of the insert section is tapered towards the proximal end of the cartridge holder and comprises a tapered section;

the drive mechanism assembled inside the body; and the cartridge assembled inside the cartridge holder.

19. The housing according to claim 1, wherein the tapered section is configured to provide a radial gap between the inside surface of the insert section and an outside surface of the cartridge.

20. The housing according to claim 1, wherein the tapered section is configured to provide an increased inner diameter of the insert section.

* * * * *

UNITED STATES PATENT AND TRADEMARK OFFICE
CERTIFICATE OF CORRECTION

PATENT NO. : 11,376,365 B2
APPLICATION NO. : 16/320519
DATED : July 5, 2022
INVENTOR(S) : Naceur Rekaya, Neal Alexander Blundred and Paul Richard Draper Page 1 of 1

It is certified that error appears in the above-identified patent and that said Letters Patent is hereby corrected as shown below:

In the Claims

Column 21, Line 12, Claim 18, delete "section" and insert -- section, --

Signed and Sealed this
Twentieth Day of September, 2022

Katherine Kelly Vidal
*Director of the United States Patent and Trademark Office*